United States Patent [19]

Lin et al.

[11] Patent Number: 5,068,451
[45] Date of Patent: Nov. 26, 1991

[54] PRODUCTION OF 3-PHENOXY PROPANAL DERIVATIVES

[75] Inventors: Ivan J. B. Lin; S. J. Jong, both of Taipei Shien, Taiwan

[73] Assignee: National Science Council, Taipei, Taiwan

[21] Appl. No.: 519,177

[22] Filed: May 4, 1990

[51] Int. Cl.$^5$ .................. C07C 47/02; C07C 45/34
[52] U.S. Cl. .................. 568/442; 568/425; 568/426; 568/630; 568/648; 568/649
[58] Field of Search ............ 568/448, 649, 640, 638, 568/426, 425, 650, 442

[56] References Cited

U.S. PATENT DOCUMENTS 4,864,061  9/1989  Cuhnen .................. 568/442

FOREIGN PATENT DOCUMENTS 0095143  8/1981  Japan .................. 568/442

*Primary Examiner*—Werren B. Lone
*Attorney, Agent, or Firm*—Bacon & Thomas

[57] ABSTRACT

A method of producing 3-phenoxy propanal derivatives of 3-phenoxy propanal derivatives of the formula

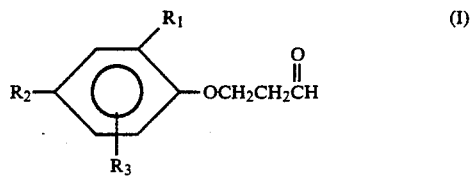
(I)

wherein $R_1$, $R_2$ and $R_3$ are —H, —$CH_3$ or a halogen radical, which comprises oxidizing allyl phenoxy ether derivatives of the formula

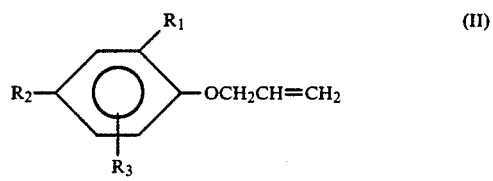
(II)

wherein $R_1$, $R_2$ and $R_3$ are as defined above, in an alcohol as a solvent in the presence of a palladium salt, an oxidant, optionally an alkali metal salt of an onganic acid, and/or an acid at a temperature of 5° C. -100° C.

11 Claims, No Drawings

PRODUCTION OF 3-PHENOXY PROPANAL DERIVATIVES

TECHNICAL FIELD OF THE INVENTION

The present invention relates to a method of producing 3-phenoxy propanol derivatives.

BACKGROUND OF INVENTION 3-phenoxy propanal can be used as an intermediate for synthesizing medicine, plasticizer, and surfactant. Due to its wide applications, lot of efforts were made to develop a new method for preparing 3-phenoxy propanal. Up to the present, all the methods used for producing this product in the art encountered the following problems: severe reaction conditions, low yields, expensive starting raw materials and complicated reaction steps. For instance, the method described in U.S. Pat. No. 2,500,582 comprising reacting acrolein with phenol in the presence of p-resorcinol and pyridine under refluxing condition for 2.5 hours. The yield of 3-phenoxy propanal is about 4%. The reaction can be described as:

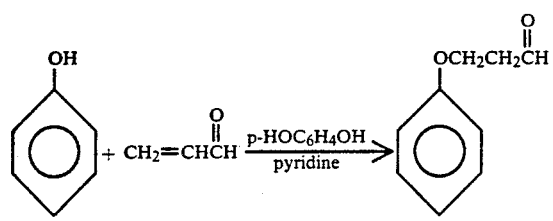

The above reaction has suffered two disadvantages: severe conditions and low yield.

An article by J. Crosby and J. M. Stirling, et al., entitled "Elimination and addition reactions, part XIX. Elimination of phenoxide from β-substituted ethyl phenyl ethers: the nature of activation in 1,2-elimination" *J. Chem. Soc.* (B), 4, 671 (1970), taught a method for preparing 3-phenoxy propanal comprising reacting 3-phenoxy propanol with $C_6H_{11}N{=}C{=}N\text{-}C_6H_{11}$ and DMSO at 20° C. for 16 hours. The yield is about 28%. The reaction can be shown as:

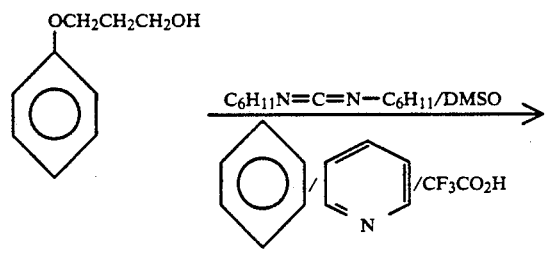

The abovementioned method also suffers disadvantages of expensive raw materials and low product yield.

A. M. Yuldashev and his coworkers in their article, entitled "Synthesis of β- and γ-hydroxyphenyl butyl ester and study of their interaction with zinc chloride", *Sint. Reakts. Sposobn. Org. Soedin*, 32 (1983); CA. 101.72565 q (1984) disclosed a process for preparing 3-phenoxy propanal comprising oxidizing the 2-phenoxy ethanol and then undergoing Grignard addition to form $PhOCH_2CH_2CHMeOH$, which upon further oxidation will produce 3-phenoxy propanal. The reaction can be described as:

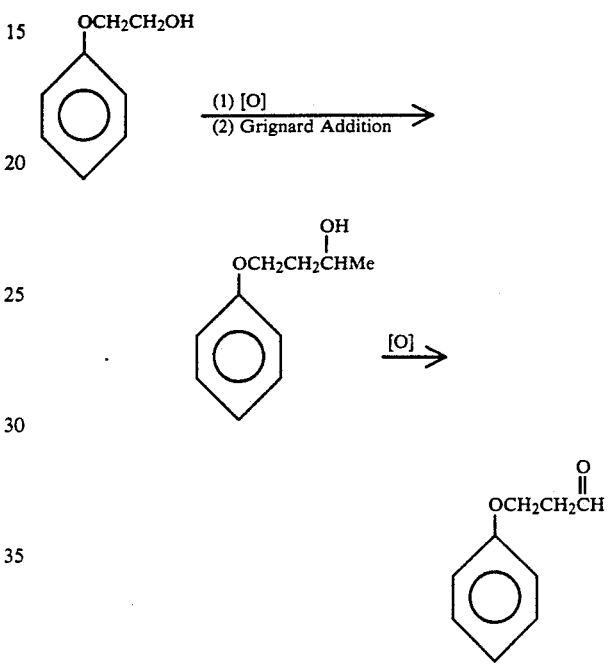

The abovementioned process involves complicated reaction steps and the overall yield is also low.

An object of the present invention is to provide a method for producing 3-phenoxy propanal derivatives.

Another object of the present invention is to provide a method for producing 3-phenoxy propanal derivatives at a very low reaction temperature (25°-50° C.) and under an open atmospheric condition without supplying additional oxygen, and have a yield about 76%.

SUMMARY OF THE INVENTION

The present invention provides a method of producing 3-phenoxy propanal derivatives of the formula

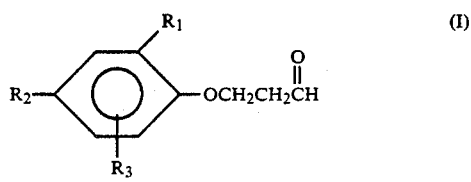

wherein $R_1$, $R_2$ and $R_3$ are —H, —$CH_3$ or a halogen radical, which comprises oxidizing allyl phenoxy ether derivatives of the formula

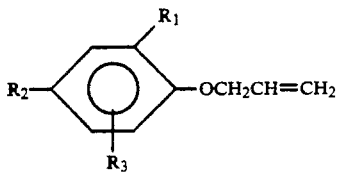

wherein $R_1$, $R_2$ and $R_3$ are as defined above, in an alcohol as a solvent in the presence of a palladium salt, an oxidant, optionally an alkali metal salt of an organic acid, and/or an acid.

DETAILED DESCRIPTION OF THE INVENTION

The present invention is related to a method of producing 3-phenoxy propanal derivatives of the formula I. This invention comprises oxidizing allyl phenoxy ether derivatives of the formula II in an alcohol as a solvent in the presence of a palladium salt, an oxidant, optionally an alkali metal salt of an organic acid, and/or an acid.

Examples of suitable allyl phenoxy ether derivatives of formula II are allyl phenoxy ether, o-methyl allyl phenoxy ether, m-methyl allyl phenoxy ether, p-methyl allyl phenoxy ether, 2,6-dimethyl allyl phenoxy ether, 2,4,6-trimethyl allyl phenoxy ether and p-chloro allyl phenoxy ether. The allyl phenoxy ether derivatives of formula II can be obtained by refluxing phenolic compounds in acetone with allyl bromide in the presence of potassium carbonate for about 6 hours.

Illustrative of the palladium salts used in the present invention are $PdCl_2$, $PdBr_2$, $PdSO_4$, $Pd(NO_3)_2$, $Li_2PdCl_4$, $Na_2PdCl_4$, $K_2PdCl_4$, and the like. Among which $PdCl_2$ is preferred. Suitable amount of this palladium salt is about 0.01–200 mol %, preferably about 10 mole %, of the starting ether.

The oxidants suitable for using in the present invention for example are copper salt complex compounds such as $CuCl_2.2H_2O$, $CuCl_2$, $CuCl$, $Cu(NO_3)_2$, $CuBr_2$, $CuBr$, and $CuSO_4$; p-benzoquinone; HPA ($H_9PMo_6V_6O_{40}$); $H_2O_2$ and t-butyl hydrogen peroxide. Among these oxidants $CuCl_2.2H_2O$ is preferred. The amount of this oxidant used in the reaction is about 0.01–1000 mole %, preferablly about 300 mole %, of the starting ether.

Examples of suitable alcohol solvents used in the present invention are methanol, ethanol, 1-propanol, 2-propanol, 1-butanol, tertiary butyl alcohol, 1,2-ethylene glycol, 1,3-propylene glycol, and a water mixture thereof. In the present invention different degrees of alcohol solvents were tested to see the effect on the reaction products. The results indicate that: the higher the degree of the alcohol solvent, the slower the reaction; hydrolysis of the acetal and ketal products obtained from the higher degree alcohol is easier than the lower one; and the product distribution tends to favor aldehyde. For example, when methanol (primary), 2-propanol (secondary), and tertiary butyl alcohol (tertiary) are used as solvent respectively, it is found that the reaction time is about 40 minutes for the methanol solvent, and about 2 hours for the 2-propanol and tertiary butyl alcohol. The major products in methanol are ketal and acetal, while in 2-propanol or tertiary butyl alcohol, the major products are aldehyde and acetone. The latter two products are obtained presumably from the hydrolysis of ketal and acetal. The tertiary butyl alcohol solvent system shows the highest product selectivity toward aldehyde. Mixing water with the alcohol solvent has a positive effect for enhancing the hydrolysis of ketal and acetal such that the yields of aldehyde and ketone increase. Suitable amount of the alcohol solvent or water/alcohol solvent used in the reaction system is ranging from 0.001 to 10000 ml, preferablly 2678–4464 ml, per mole of the starting ether.

The optional alkali metal salt of an organic acid used in the present invention comprises sodium acetate, potassium acetate, sodium salt of propionic acid, potassium salt of propionic acid, sodium butyrate, potassium butyrane, sodium benzoate, and potassium benzoate, and preferablly sodium acetate is used. Suitable molar ratio of said salt to the starting ether is ranging from 0.01 to 1000%, preferablly 40–500%.

The acids useful in the present invention include organic and inorganic acid, such as acetic acid, propionic acid, butanoic acid, benzoic acid, hydrogen chloride, phosphoric acid, sulfuric acid and nitric acid. The preferable acid is acetic acid. Suitable amount of this acid may range from 0.001 to 10000 ml, preferablly 800–1000 ml, per mole of the starting ether.

In the present invention, the reaction is slow in the absence of the alkali metal salt of an organic acid and the acid. The addition of said alkali metal salt of an organic acid or said acid or both of them will increase the reaction rate. In one of the embodiments, the conversion of allyl phenyl ether is zero when $PdCl_2/CuCl_2.2H_2O$ (1:30 mole ratio) and allyl phenyl ether in alcohol solvent is maintained at 25° C. for 24 hours. The conversion increases to 51% as the temperature raised to 50° C. and for 1.5 hours of reaction time. However, when adding acetic acid and sodium acetate into the reaction mixture, the conversion reaches 98% for 4.5 hours of reaction time at 25° C. When only sodium acetate is added, the conversion is 100% for 45 minutes of reaction time at 50° C. As the temperature or the amount of sodium acetate is varied independently, it is noticed that the reaction rate decreases as the temperature decreases, but the selectivity for the desired product increases. When the amount of sodium acetate increases, the reaction rate will increase and selectivity for the desired product decreases. By adjusting the reaction temperature and the amount of sodium acetate added, one can find an optimal reaction condition in terms of the reaction rate and selectivity.

In the present invention, the reaction can be carried out at a temperature of about 5° C. to about 100° C., preferably between 25° to 30° C. The pressure has a minor effect on the reaction. Normally, the reaction is carried out at 1 to 10 atm, preferably under the atmospheric pressure.

Details of the present invention can be further understood by the following examples, which are meant to illustrate the present invention and are not meant to be limiting.

EXAMPLE 1

The purpose of this example is to illustrate the preparation of allyl phenyl ether derivatives which are useful as the starting ether in the present invention.

0.1 mole of phenolic compound, 0.1 mole of $K_2CO_3$, and 0.1 mole of allyl bromide were mixed with 200 ml of acetone in a flask and the mixture was heated under refluxing for 6 hours. After being cooled to room temperature, the content of the flask was poured into 200 ml water and then extracted with ethyl ether. The extract was washed with saturated aqueous sodium hydroxide solution twice, and then with water five times. After drying by magnesium sulfate, filtering, and removing the solvent, the allyl phenyl ether derivatives were obtained. The results are listed in the following Table 1.

TABLE 1

Yields of allyl phenyl ether derivatives

| Phenolic Compounds | Yields (%) | allyl phenyl ether derivatives |
|---|---|---|
| phenol | 90 | allyl phenyl ether |
| o-methyl phenol | 80 | o-methyl allyl phenyl ether |
| m-methyl phenol | 83 | m-methyl allyl phenyl ether |
| p-methyl phenol | 85 | p-methyl allyl phenyl ether |
| 2,6-dimethyl phenol | 34 | 2,6-dimethyl allyl phenyl ether |
| 2,4,6-trimethyl phenol | 20 | 2,4,6-trimethyl allyl phenyl ether |
| p-chloro phenol | 77 | p-chloro allyl phenyl ether |

EXAMPLE 2

In this example, allyl phenol ether was oxidized in methanol in the presence of $PdCl_2/CuCl_2 \cdot 2H_2O$ (1:30, mole ratio) at 25° C. and 50° C. respectively. The effects of sodium acetate and acetic acid concentration in methanol on the oxidation of allyl phenyl ether were examined.

0.1 g (0.56 mmole) of $PdCl_2$, 2.87 g (16.8 mmole) of $CuCl_2 \cdot 2H_2O$, and optionally 16.8 mmole of sodium acetate were introduced into a 100 ml flask. Methanol, 5.6 mmole of allyl phenyl ether, and optionally 5 ml of acetic acid were added into the flask to start the reaction. The reaction temperature was set to be 25° C. or 50° C. The reaction products were obtained by extraction with ether. The conditions and results are listed in Table 2.

TABLE 2

The effects of the sodium acetate and acetic acid concentrations on the oxidation of allyl phenyl ether at 25° C. or 50° C. in the presence of $PdCl_2/CuCl_2 \cdot 2H_2O$ (1:30 mole ratio) in methanol solvent

| NaOAc mM | HOAc/ Methanol ml/ml | Conversion (time) % | Temp °C. | Product(i) | Selectivity % |
|---|---|---|---|---|---|
| — | 0/20 | —0(24 hr) | 25 | — | — |
| 16.8 | 0/20 | 98(4.5 hr) | 25 | acetal | 50 |
|  |  |  |  | ketal | 40 |
|  |  |  |  | ketone | 8 |
| 16.8 | 5/15 | 95(6 hr) | 25 | acetal | 40 |
|  |  |  |  | ketal | 40 |
|  |  |  |  | ketone | 19 |
| — | 0/20 | 51(1.5 hr) | 50 | acetal | 68 |
|  |  |  |  | ketal | 15 |
|  |  |  |  | ketone | 15 |
| 16.8 | 0/20 | 100(40 min.) | 50 | acetal | 34 |
|  |  |  |  | ketal | 52 |
|  |  |  |  | ketone | 13 |
| 16.8 | 5/15 | 100(40 min.) | 50 | acetal | 34 |
|  |  |  |  | ketal | 51 |
|  |  |  |  | ketone | 14 |

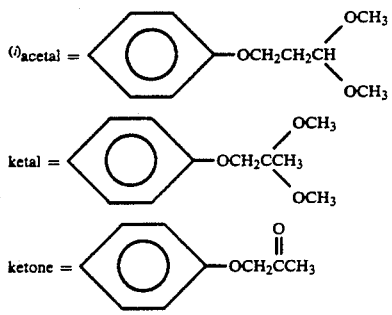

From Table 2, it is found that the major products of the reaction carried out in methanol are ketal and acetal, wherein some of the ketal is hydrolyzed into ketone and no acetal is hydrolyzed. The selectivity for acetal will increase if the reaction takes place in the absence of sodium acetate or sodium acetate/acetic acid, namely 68% selectivity at 50° C. In the presence of sodium acetate or sodium acetate/acetic acid in the reaction system, the acetal selectivity at 50° C. is lower than 25° C. reaction temperature.

EXAMPLE 3

The procedures of the above Example 2 were repeated, except that the methanol solvent was replaced by a mixture of methanol/water, and 1.38 g (16.8 mmole) sodium acetate and 5 ml of acetic acid were used in this example. The conditions and results are listed in Table 3.

TABLE 3

The effects of methanol/water ratio on the oxidation of allyl phenyl ether in the presence of $PdCl_2/CuCl_2 \cdot 2H_2O$, sodium acetate and acetic acid

| Methanol ml | Water ml | Temp °C. | Conversion (Time) % | Product(i) | Selectivity % |
|---|---|---|---|---|---|
| 20 |  | 50 | 100 (40 min.) | acetal | 34 |
|  |  |  |  | ketal | 51 |
|  |  |  |  | ketone | 14 |
| 5 | 15 | 50 | 99 (2.5 hr) | acetal | 8 |
|  |  |  |  | ketone | 67 |
|  |  |  |  | 3-phenoxy propanal | 23 |
| 1 | 19 | 50 | 99 (3.5 hr) | ketone | 49 |
|  |  |  |  | phenol | 29 |
|  |  |  |  | 3-phenoxy propanal | 20 |
| 10 | 10 | 90 | 97 (20 min.) | ketone | 46 |
|  |  |  |  | 3-phenoxy propanal | 50 |
| 5 | 15 | 90 | 93 (30 min.) | ketone | 39 |
|  |  |  |  | phenol | 39 |
|  |  |  |  | 3-phenoxy propanal | 20 |

(i)The acetal, ketal and ketone are defined as those in Table 2.

From Table 3, it is quite obvious that the addition of water in the reaction system will decrease the reaction rate and enhance the hydrolysis of acetal and ketal to produce aldehyde and ketone. However, as the water content increases, especially at a higher temperature, the ether will undergo bond cleavage to yield phenol.

EXAMPLE 4

In this example various alcohol solvents were used in the oxidation of allyl phenyl ether at 50° C.

0.1 g (0.56 mmole) of $PdCl_2$, 2.87 g (16.8 mmole) of $CuCl_2.2H_2O$ and 1.38 g (16.8 mmole) of sodium acetate were introduced to a 100 ml flask. 20 ml of alcohol solvent and 5.6 mmole of allyl phenyl ether were added into the flask with stirring and the temperature was maintained at 50° C. The reaction products were then extracted with ethyl ether. The conditions and the results are listed in Table 4.

TABLE 4

Oxidation of allyl phenyl ether in various types of alcohol solvent at 50° C. in the presence of $PdCl_2/CuCl_2.2H_2O$.

| Alcohol | Conversion (%) (Time) | Product(i) | Selectivity (%) |
|---|---|---|---|
| methanol | 100 (40 min.) | acetal | 34 |
|  |  | ketal | 52 |
|  |  | ketone | 13 |
| 2-propanol | 100 (2 hr) | ketone | 44 |
|  |  | 3-phenoxy propanal | 54 |
| tertiary butyl alcohol | 100 (2 hr) | ketone | 32 |
|  |  | 3-phenoxy propanal | 65 |

(i)The acetal, ketal and ketone are defined as those in Table 2.

Table 4 shows that the reaction rate decreases as the alcohols change from primary to tertiary; however, the selectivity of 3-phenoxy propanol increases.

EXAMPLE 5

This example shows the effects of both the reaction temperature and the amount of sodium acetate used on the oxidation of allyl phenyl ether.

0.1 g (0.56 mmole) of $PdCl_2$, 2.87 g (16.8 mmole) of $CuCl_2.2H_2O$ and sodium acetate were introduced to a 100 ml flask. 20 ml of tertiary butyl alcohol and 5.6 mmole of allyl phenyl ether were added into the flask to start the reaction. The reaction products were then extracted with ethyl ether. The conditions and the results are listed in Table 5.

TABLE 5

The effects of reaction temperature and amount of sodium acetate used on the oxidation of allyl phenyl ether in tertiary butyl alcohol in the presence of $PdCl_2/CuCl_2.2H_2O$

| NaOAc mM | Temp. °C. | Conversion (Time) % | Product(i) | Selectivity % |
|---|---|---|---|---|
| 16.8 | 50 | 100 (2 hr) | 3-phenoxy propanal | 65 |
|  |  |  | ketone | 32 |
| 13.4 | 50 | 99 (3 hr) | 3-phenoxy propanal | 68 |
|  |  |  | ketone | 29 |
| 6.7 | 30 | 93 (24 hr) | 3-phenoxy propanal | 81 |
|  |  |  | ketone | 17 |
| 16.8 | 25 | 100 (24 hr) | 3-phenoxy propanal | 65 |
|  |  |  | ketone | 34 |
| 13.4 | 25 | 98 (24 hr) | 3-phenoxy propanal | 73 |
|  |  |  | ketone | 25 |

(i)The ketone is defined as in Table 2.

Table 5 shows that by adjusting the amount of sodium acetate used and the reaction temperature, one can obtain a desired reaction conversion and selectivity.

EXAMPLE 6

This example illustrates that the derivatives of allyl phenyl ether can also be used in the present invention.

0.1 g (0.56 mmole) of $PdCl_2$, 2.87 g (16.8 mmole) of $CuCl_2.2H_2O$ and 1.1 g (13.4 mmole) of sodium acetate were introduced into a 100 ml flask. 20 ml of tertiary butyl alcohol and 5.6 mmole of allyl phenyl ether derivatives were added to start the reaction at 25° C. The reaction products are extracted with ethyl ether. The conditions and the results are listed in Table 6.

TABLE 6

| Reactants | Conversion % | Product | Selectivity % |
|---|---|---|---|
| allyl phenyl ether | 98 | 3-phenoxy propanal | 73 |
|  |  | phenoxy propanone | 25 |
| o-methyl allyl ether | 96 | 3-(o-methyl phenoxy) propanal | 73 |
|  |  | o-methyl phenoxy propanone | 25 |
| m-methyl allyl phenyl ether | 94 | 3-(m-methyl phenoxy) propanal | 68 |
|  |  | m-methyl phenoxy propanone | 29 |
| p-methyl allyl phenyl ether | 92 | 3-(p-methyl phenoxy) propanal | 71 |
|  |  | p-methyl phenoxy propanone | 26 |
| 2,6-dimethyl allyl phenyl ether | 94 | 3-(2,6-dimethyl phenoxy) propanal | 71 |
|  |  | 2,6-dimethyl phenoxy propanone | 27 |
| 2,4,6-trimethyl allyl phenyl ether | 95 | 3-(2,4,6-trimethyl phenoxy) propanal | 55 |
|  |  | 2,4,6-trimethyl phenoxy propanone | 43 |
| p-chloro allyl phenyl ether | 52 | 3-(p-chloro phenoxy) propanal | 85 |
|  |  | p-chloro phenoxy propanone | 15 |

What is claimed is:

1. A method of 3-phenoxy propanal derivatives of the formula

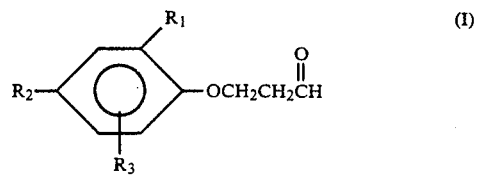

(I)

wherein $R_1$, $R_2$ and $R_3$ are —H, —$CH_3$ or a halogen radical, which method comprises oxidizing allyl phenoxy ether derivatives of the formula

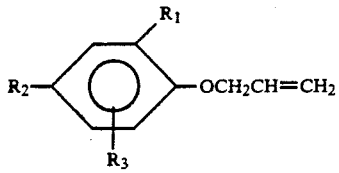

wherein $R_1$, $R_2$ and $R_3$ are as defined above, in an alcohol as a solvent in the presence of a palladium salt, a copper salt complex oxidant, an alkali metal salt of an organic acid, and an acid at a temperature of 5° C.–100° C. and at a pressure from atmospheric pressure to 10 atm.

2. A method in accordance with claim 1, wherein said palladium salt is selected from the group consisting of $PdCl_2$, $PdBr_2$, $PdSO_4$, $Pd(NO_3)_2$, $Li_2PdCl_4$, $Na_2PdCl_4$ and $K_2PdCl_4$.

3. A method in accordance with claim 1, wherein said oxidant is $CuCl_2.2H_2O$.

4. A method in accordance with claim 1, wherein said alkali metal salt of an organic acid is selected from the group consisting of sodium acetate, potassium acetate, sodium salt of propionic acid, potassium salt of propionic acid, sodium butyrate, potassium butyrate, sodium benzoate and potassium benzoate.

5. A method in accordance with claim 1, wherein said acid is selected from the group consisting of acetic acid, propionic acid, butanoic acid, benzoic acid, hydrogen chloride, phosphoric acid, sulfuric acid and nitric acid.

6. A method in accordance with claim 1, wherein said alcohol solvent is selected from the group consisting of methanol, ethanol, 1-propanol, 2-propanol, 1-butanol, 2-butanol, tertiary butyl alcohol, 1,2-ethylene glycol, 1,3-dihydroxy propane and a water mixture thereof.

7. A method in accordance with claim 1, wherein the temperature is 25°–30° C.

8. A method of producing 3-phenoxypropanal derivatives of the formula

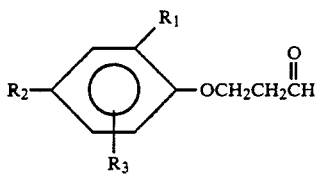

wherein $R_1$, $R_2$, and $R_3$ are —H, —$CH_3$ or a halogen radical, which method comprises oxidizing allyl phenoxy ether derivatives of the formula

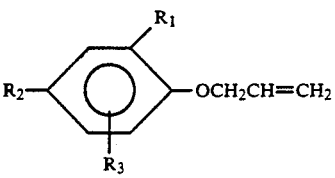

wherein $R_1$, $R_2$ and $R_3$ are as defined above, in an alcohol as a solvent in the presence of a palladium salt, a copper salt complex oxidant, and an acid at a temperature of 5° C.–100° C. and at a pressure from atmospheric pressure to 10 ATM.

9. A method of producing 3-phenoxypropanal derivatives of the formula

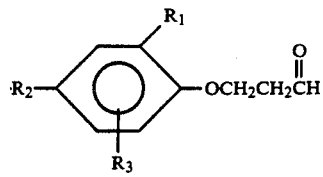

wherein $R_1$, $R_2$, and $R_3$ are —H, —$CH_3$ or a halogen radical, which method comprises oxidizing allyl phenoxy ether derivatives of the formula

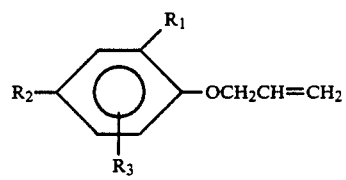

wherein $R_1$, $R_2$ and $R_3$ are as defined above, in an alcohol as a solvent in the presence of a palladium salt, a copper salt complex oxidant, and an alkali metal salt of an organic acid, at a temperature of 5° C.–100° C. and at a pressure from atmospheric pressure to 10 ATM.

10. A method of producing 3-phenoxypropanal derivatives of the formula

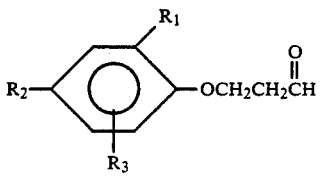

wherein $R_1$, $R_2$, and $R_3$ are —H, —$CH_3$ or a halogen radical, which method comprises oxidizing allyl phenoxy ether derivatives of the formula

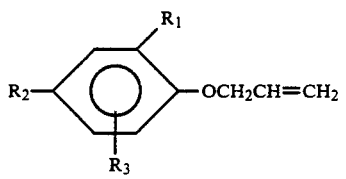

wherein $R_1$, $R_2$ and $R_3$ are as defined above, in an alcohol as a solvent in the presence of a palladium salt, and a copper salt complex oxidant, at a temperature of 5° C.–100° C. and at a pressure from atmospheric pressure to 10 ATM.

11. A method in accordance with claim 8, wherein said acid is selected from the group consisting of acetic acid, propionic acid, butanoic acid, benzoic acid, hydrogen chloride, phosphoric acid, sulfuric acid and nitric acid.

* * * * *